(12) United States Patent
Castelhano et al.

(10) Patent No.: US 8,557,814 B2
(45) Date of Patent: *Oct. 15, 2013

(54) MTOR INHIBITOR SALT FORMS

(75) Inventors: Arlindo L. Castelhano, New City, NY (US); Kristen Michelle Mulvihill, Dix Hills, NY (US); Gary C. Visor, Castro Valley, CA (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 135 days.

This patent is subject to a terminal disclaimer.

(21) Appl. No.: 12/922,928

(22) PCT Filed: Mar. 18, 2009

(86) PCT No.: PCT/US2009/037505
§ 371 (c)(1),
(2), (4) Date: Sep. 16, 2010

(87) PCT Pub. No.: WO2009/117482
PCT Pub. Date: Sep. 24, 2009

(65) Prior Publication Data
US 2011/0015197 A1    Jan. 20, 2011

Related U.S. Application Data

(60) Provisional application No. 61/070,062, filed on Mar. 19, 2008.

(51) Int. Cl.
*A61K 31/53* (2006.01)
*C07D 487/04* (2006.01)

(52) U.S. Cl.
USPC .......................... 514/243; 544/184

(58) Field of Classification Search
USPC .......................... 514/243; 544/184
See application file for complete search history.

(56) References Cited

U.S. PATENT DOCUMENTS

| | | | |
|---|---|---|---|
| 5,869,485 A | 2/1999 | Missbach | |
| 6,001,839 A | 12/1999 | Calderwood | |
| 7,700,594 B2 * | 4/2010 | Chen et al. | 514/243 |
| 2002/0156081 A1 | 10/2002 | Hirst | |
| 2003/0073218 A1 | 4/2003 | Shokat | |
| 2003/0187001 A1 | 10/2003 | Calderwood | |
| 2005/0004142 A1 | 1/2005 | Adams | |
| 2005/0130994 A1 | 6/2005 | Chen | |
| 2006/0019957 A1 | 1/2006 | Crew | |
| 2006/0084654 A1 | 4/2006 | Beck | |
| 2006/0235031 A1 | 10/2006 | Arnold | |
| 2007/0112005 A1 | 5/2007 | Chen | |
| 2007/0149521 A1 | 6/2007 | Crew | |
| 2007/0167383 A1 | 7/2007 | Roberts | |
| 2007/0203143 A1 | 8/2007 | Sheppard | |
| 2007/0254883 A1 | 11/2007 | Crew | |
| 2007/0280928 A1 | 12/2007 | Buck | |
| 2007/0293516 A1 | 12/2007 | Knight | |
| 2008/0032960 A1 | 2/2008 | Knight | |
| 2009/0099174 A1 | 4/2009 | Smith | |
| 2009/0124638 A1 | 5/2009 | Shokat | |
| 2009/0163468 A1 | 6/2009 | Chen | |
| 2009/0263397 A1 | 10/2009 | Buck | |
| 2009/0274698 A1 | 11/2009 | Bhagwat | |
| 2010/0099679 A1 | 4/2010 | Chen | |
| 2011/0015197 A1 | 1/2011 | Castelhano | |

FOREIGN PATENT DOCUMENTS

| | | |
|---|---|---|
| WO | 2007115620 A2 | 10/2007 |
| WO | 2007126841 A2 | 11/2007 |
| WO | 2011014726 A2 | 7/2010 |
| WO | 2011005909 A2 | 1/2011 |

OTHER PUBLICATIONS

Philip L. Gould, International Journal of Pharmaceuticals 33, (1986) 201-217.*
Bergstrom, D. et al. (1981) Journal of Organic Chemistry 46(7):1423-1431.
Bergstrom, D. et al. (1991) Journal of Organic Chemistry 56(19):5598-5602.
Bishop, A. et al. (1999) Journal of the American Chemical Society 121(4):627631.
Buzko, O. et al. (2002) Journal of Computer-Aided Design 16(2):113-127.
Database Beilstein—Beilstein Institute for Organic Chemistry, Frankfurt-Main, DE XP002449941. Database accession Nos. 4560199, 4563868, 4573145, 4589920 (BRNs). Abstract (This document included in 10052 ISR attached to Bergstrom 1423. Bergstrom ref cited for OS-10052, but not Database Beilstein).
Database Beilstein—Beilstein Institute for Organic Chemistry, Frankfurt-Main, DE XP002449942. Database accession Nos. 759552, 7598012, 7598776, 7599702, 7601233, 7604323, 8071040, 8075363, 8077883, 8082219, 8086506, 8088093, 8572470, 8574862, 8581421, 8596325 (BRNs). abstract (This document (Continued)

*Primary Examiner* — James O Wilson
*Assistant Examiner* — Ebenezer O Sackey
(74) *Attorney, Agent, or Firm* — Frank W. Forman; Astellas US LLC

(57) ABSTRACT

Salt forms of mTOR inhibitors of the Formula (I):

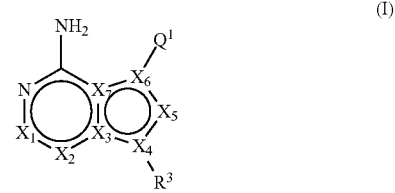

and methods of preparation, formulation, and use in treating disease.

18 Claims, 2 Drawing Sheets

(56) References Cited

OTHER PUBLICATIONS included in 10052 ISR attached to Seela 910. Bergstrom ref cited for OS-10052, but not Database Beilstein).
Hubbard, R.D. et al. (2007) Bioorganic & Medicinal Chemistry Letters 17(19):5406-5409.
International Preliminary Report on Patentability in PCT/US2009/037505.
International Search Report in PCT/US2009/037505.
Kinkade, C.W. et al. (2008) Journal of Clinical Investigation 118(9):3051-3064.
Legrier, M. et al. (2007) Cancer Research 67(23):11300-11308.
Papadimitrakopoulou, V. and Adjei, A.A. (2006) Journal of Thoracic Oncology 1(7): 749-751.
Prousek, J. (1984) Collection of Czechoslovak Chemical Communications 49(8):1788-1794.
Raslan, M.A. et al. (2000) Heteroatom Chemistry 11(2):94-201.
Seela, F. et al. (2000) Helvetica Chimica Acta 83(5):910-927.
Schram, K. et al. (1974) Journal of Carbohydrates, Nucleosides, Nucleotides 1(1):39-54.

* cited by examiner

MTOR INHIBITOR SALT FORMS

This application claims priority of U.S. Appl. No. 61/070,062 (Mar. 19, 2008), the content of which is incorporated herein in its entirety by this reference.

BACKGROUND

The present invention is directed to bicyclic compounds that are inhibitors of mammalian Target Of Rapamycin (mTOR) kinase (also known as FRAP, RAFT, RAPT, SEP). In particular, the present invention is directed to fused bicyclic compounds that are mTOR inhibitors useful in the treatment of cancer.

It has been shown that high levels of dysregulated mTOR activity are associated with a variety of human cancers and several hamartoma syndromes, including tuberous sclerosis complex, the PTEN-related hamartoma syndromes and Peutz-Jeghers syndrome. Although rapamycin analogues are in clinical development for cancer as mTOR kinase inhibitors, the clinical out come with CCI-779 is just modest in breast and renal cancer patients. This is probably because rapamycin partially inhibits mTOR function through raptor-mTOR complex (mTORC1). It has been also found that ⅔ of the breast cancer and ½ of renal cancer patients are resistant to rapamycin therapy. With a recent discovery of rictor-mTOR complex (mTORC2) which is involved in phosphorylation of AKT (S473) that is important in regulation of cell survival and modulation of PKCα that plays a major role in regulation of actin cytoskeletal organization in a rapamycin-independent manner, and inhibition of these activities of mTOR is probably important for broader antitumor activity and better efficacy. Therefore, it is desirable to develop novel compounds that are direct inhibitors of mTOR kinase, which would inhibit mTORC1 and mTORC2.

With the recent discovery of rapamycin independent function of mTOR (by mTOR2) in phosphorylation AKT (at S473) that is important in regulation of cell survival and modulation of PKCα, which plays a major role in regulation of actin cytoskeletal organization, it is believed that inhibition of mTOR function by rapamycin is partial. Therefore, discovery of a direct mTOR kinase inhibitor, which would completely inhibit the function of both mTORC1 and mTORC2, is required for broader anti-tumor activity and better efficacy. Here we describe the discovery of direct mTOR kinase inhibitors, which can be used in the treatment of a variety of cancers—including breast, lung, kidney, prostate, blood, liver, ovarian, thyroid, GI tract and lymphoma—and other indications such as rheumatoid arthritis, hamartoma syndromes, transplant rejection IBD, multiple sclerosis and immunosuppression.

Recent success of Tarceva, an EGFR kinase inhibitor for the treatment of NSCLC, and prior success with Gleevec for the treatment of CML indicate that it is possible to develop selective kinase inhibitors for the effective treatment of cancers. Although there are several anti-cancer agents including kinase inhibitors, there is still continuing need for improved anti-cancer drugs, and it would be desirable to develop new compounds with better selectivity, potency or with reduced toxicity or side effects. Thus, it is desirable to develop compounds that exhibit mTOR inhibition in order to treat cancer patients. Further, such compounds may be active in other kinases such as, for example, PI3K, Src, KDR, to add efficacy in breast, non-small cell lung cancer (NSCLC), renal cell carcinoma, mantle cell lymphoma, endometrial cancers, or other hamartoma syndromes.

With respect to new salt forms, it is desirable, that they provide a favorable profile with respect to pharmaceutical manufacture, formulation, storage, and use. For example, it is desirable; that the salt exhibit favorable solubility, hygroscopicity, stability, uniformity, reproducibility, purity, among other known criteria.

US2007/0112005 discloses, inter alia, mTOR inhibiting compounds. The present invention relates to particular salts and forms of mTOR inhibitor compounds, their preparation, formulation, and use.

SUMMARY OF THE INVENTION

In some aspects, the present invention provides salts and polymorphs of compounds represented by Formula (I):

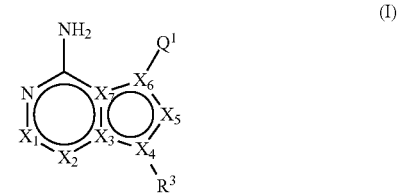

as described and detailed further below. The salts can be prepared from the compounds described in US2007/0112005, which also describes their preparation, biological activity, and use. US2007/0112005 is incorporated by reference herein in its entirety. The invention includes the salts, polymorphs, their preparation, formulation, and use to treat disease.

DETAILED DESCRIPTION OF THE INVENTION

Figure 1:
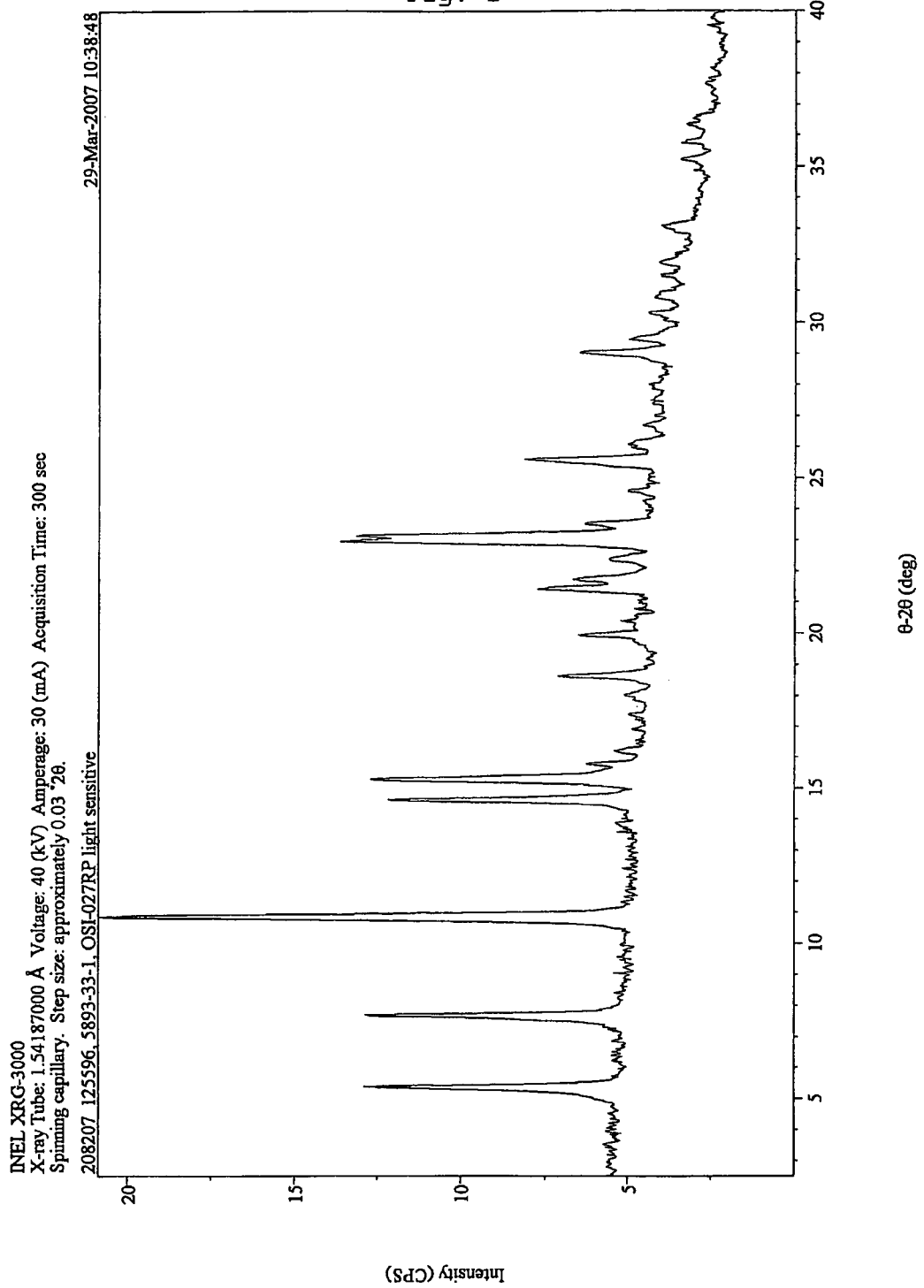
FIG. 1: XRPD pattern of Example 1 tromethamine salt form.

In some aspects, the invention provides pharmaceutically acceptable salts of a compound represented by Formula (I):

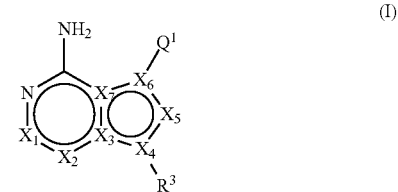

wherein:
$X_1$, and $X_2$ are each independently N or C-$(E^1)_{aa}$;
$X_5$ is N, C-$(E^1)_{aa}$, or N-$(E^1)_{aa}$;
$X_3$, $X_4$, $X_6$, and $X_7$ are each independently N or C;
wherein at least one of $X_3$, $X_4$, $X_5$, $X_6$, and $X_7$ is independently N or N-$(E^1)_{aa}$;
$R^3$ is $C_{0-10}$alkyl, cyclo$C_{3-10}$alkyl, aminomethylcyclo $C_{3-10}$alkyl, bicyclo$C_{5-10}$alkyl, aryl, heteroaryl, aralkyl, heteroaralkyl, heterocyclyl or heterobicyclo$C_{5-10}$alkyl any of which is optionally substituted by one or more independent $G^{11}$ substituents;

$Q^1$ is -A($R^1$)$_m$B(W)$_n$ or -B($G^{11}$)$_n$A(Y)$_m$;

A and B are respectively, 5 and 6 membered aromatic or heteroaromatic rings, fused together to form a 9-membered heteroaromatic system excluding 5-benzo[b]furyl and 3-indolyl; and excluding 2-indolyl, 2-benzoxazole, 2-benzothiazole, 2-benzimidazolyl, 4-aminopyrrolopyrimidin-5-yl, 4-aminopyrrolopyrimidin-6-yl, and 7-deaza-7-adenosinyl derivatives when $X_1$ and $X_5$ are CH, $X_3$, $X_6$ and $X_7$ are C, and $X_2$ and $X_4$ are N;

or $Q^1$ is -A($R^1$)$_m$A(Y)$_m$, wherein each A is the same or different 5-membered aromatic or heteroaromatic ring, and the two are fused together to form an 8-membered heteroaromatic system;

$R^1$ is independently, hydrogen, —N($C_{0-8}$alkyl)($C_{0-8}$alkyl), hydroxyl, halogen, oxo, aryl(optionally substituted with 1 or more $R^{31}$ groups), hetaryl(optionally substituted with 1 or more $R^{31}$ groups), $C_{1-6}$alkyl, —$C_{0-8}$alkyl$C_{3-8}$cycloalkyl, —$C_{0-8}$alkyl-NR$^{311}$S(O)$_{0-2}$R$^{321}$, —$C_{0-8}$alkyl-NR$^{311}$S(O)$_{0-2}$NR$^{321}$R$^{331}$, —$C_{0-8}$alkyl-S(O)$_{0-2}$NR$^{311}$R$^{321}$, —$C_{0-8}$alkyl-NR$^{311}$COR$^{321}$, —$C_{0-8}$alkyl-NR$^{311}$CO$_2$R$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CON(R$^{311}$)S(O)$_{0-2}$R$^{321}$, —$C_{0-8}$alkyl-CO$_2$R$^{311}$, —$C_{0-8}$alkyl-S(O)$_{0-2}$R$^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocyclyl, —$C_{0-8}$alky-O—$C_{0-8}$alkylaryl, —$C_{0-8}$alkylaryl, —$C_{0-8}$alkylhetaryl, —$C_{0-8}$alkylheterocyclyl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocyclyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{311}$)—$C_{0-8}$alkyl, —$C_{0-8}$alkyl-N(R$^{311}$)—$C_{0-8}$alkyl$C_{3-8}$cycloalkyl, —$C_{0-8}$alkyl-N(R$^{311}$)—$C_{0-8}$alkylheterocyclyl, —$C_{0-8}$alkyl-N(R$^{311}$)—$C_{0-8}$alkylaryl, —$C_{0-8}$alkyl-N(R$^{311}$)—$C_{0-8}$alkylhetaryl, —$C_{0-8}$alkyl-NR$^{311}$R$^{321}$, —$C_{2-8}$alkenyl, —$C_{2-8}$alkynyl, NO$_2$, CN, CF$_3$, OCF$_3$, OCHF$_2$; provided that $Q^1$ is not N-methyl-2-indolyl, N-(phenylsulfonyl)-2-indolyl, or N-tert-butoxycarbonyl;

W is independently, hydrogen, —N($C_{0-8}$alkyl)($C_{0-8}$alkyl), hydroxyl, halogen, oxo, aryl(optionally substituted with 1 or more $R^{31}$ groups), hetaryl(optionally substituted with 1 or more $R^{31}$ groups), $C_{1-6}$alkyl, —$C_{0-8}$alkyl $C_{3-8}$cycloalkyl, —$C_{0-8}$alkyl-NR$^{312}$S(O)$_{0-2}$R$^{322}$, —$C_{0-8}$alkyl-NR$^{311}$S(O)$_{0-2}$NR$^{321}$R$^{331}$, —$C_{0-8}$alkyl-NR$^{311}$CO$_2$R$^{321}$, —$C_{0-8}$alkyl-CON(R$^{311}$)S(O)$_{0-2}$R$^{321}$, —$C_{0-8}$alkyl-S(O)$_{0-2}$NR$^{312}$R$^{322}$,—$C_{0-8}$alkyl-NR$^{312}$COR$^{322}$, —$C_{0-8}$alkyl-NR$^{312}$CONR$^{322}$R$^{332}$, —$C_{0-8}$alkyl-CONR$^{312}$R$^{322}$, —$C_{0-8}$alkyl-CO$_2$R$^{312}$, —$C_{0-8}$alkylS(O)$_{0-2}$R$^{312}$, —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocycloalkyl, —$C_{0-8}$alkyl-O—$C_{0-8}$alkylaryl, —$C_{0-8}$alkylaryl, —$C_{0-8}$alkylhetaryl, —$C_{0-8}$alkylheterocyclyl, —Oaryl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{312}$)—$C_{0-8}$alkyl, —$C_{0-8}$alkyl-N(R$^{312}$)—$C_{0-8}$alkyl$C_{0-8}$cycloalkyl, —$C_{0-8}$alkyl-N(R$^{312}$)—$C_{0-8}$alkylheterocycloalkyl, —$C_{0-8}$alkyl-N(R$^{312}$)—$C_{0-8}$alkylaryl, —$C_{0-8}$alkyl-N(R$^{312}$)—$C_{0-8}$alkylhetaryl, $C_{0-8}$alkyl-NR$^{312}$R$^{322}$, —$C_{2-8}$alkenyl, —$C_{2-8}$alkynyl, NO$_2$, CN, CF$_3$, OCF$_3$, OCHF$_2$; provided that $Q^1$ is not 4-benzyloxy-2-indolyl;

Y is independently, hydrogen, —N($C_{0-8}$alkyl)($C_{0-8}$alkyl), hydroxyl, halogen, oxo, aryl(optionally substituted with 1 or more $R^{31}$ groups), hetaryl(optionally substituted with 1 or more $R^{31}$ groups), $C_{0-6}$alkyl, —$C_{0-8}$alkyl$C_{3-8}$cycloalkyl, —$C_{0-8}$alkyl-NR$^{311}$S(O)$_{0-2}$R$^{321}$, —$C_{0-8}$ alkyl-NR$^{311}$S(O)$_{0-2}$NR$^{321}$R$^{331}$, —$C_{0-8}$alkyl-CON(R$^{311}$)S(O)$_{0-2}$R$^{321}$, —$C_{0-8}$alkyl-S(O)$_{0-2}$NR$^{311}$R$^{321}$, —$C_{0-8}$ alkyl-NR$^{311}$COR$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CO$_2$R$^{311}$, —$C_{0-8}$alkylS(O)$_{0-2}$R$^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocycloalkyl, —$C_{0-8}$alkyl-O—$C_{0-8}$alkylaryl, —$C_{0-8}$alkylaryl, —$C_{0-8}$alkylhetaryl, —$C_{0-8}$alkylheterocyclyl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{311}$)—$C_{0-8}$alkyl, —$C_{0-8}$alkyl-N(R$^{311}$)—$C_{0-8}$alkyl$C_{3-8}$cycloalkyl, —$C_{0-8}$alkyl-N(R$^{311}$)—$C_{0-8}$alkylheterocycloalkyl, —$C_{0-8}$alkyl-N(R$^{311}$)—$C_{0-8}$alkylaryl, —$C_{0-8}$alkyl-N(R$^{311}$)—$C_{0-8}$alkylhetaryl, —$C_{0-8}$alkyl-NR$^{311}$R$^{321}$, —$C_{2-8}$alkenyl, —$C_{2-8}$alkynyl, NO$_2$, CN, CF$_3$, OCF$_3$, OCHF$_2$; provided that $Q^1$ is not 2-carboxy-5-benzo[b]thiophenyl;

$G^{11}$ is halo, oxo, —CF$_3$, —OCF$_3$, —OR$^{312}$, —NR$^{312}$R$^{322}$, —C(O)R$^{312}$, —C(O)C$_{3-8}$cycloalkyl, —CO$_2$C$_{3-8}$cycloalkyl, —CO$_2$R$^{312}$, —C(=O)NR$^{312}$R$^{322}$, —NO$_2$, —CN, —S(O)$_{0-2}$R$^{312}$, —SO$_2$NR$^{312}$R$^{322}$, NR$^{312}$C(=O)R$^{322}$, NR$^{312}$C(=O)OR$^{322}$, NR$^{312}$C(=O) NR$^{322}$R$^{332}$, NR$^{312}$S(O)$_{0-2}$R$^{322}$, —C(=S)OR$^{312}$, —C(=O)SR$^{312}$, —NR$^{312}$C(=NR$^{322}$)NR$^{332}$R$^{341}$, —NR$^{312}$C(=NR$^{322}$)OR$^{332}$, NR$^{312}$C(=NR$^{322}$)SR$^{332}$, —OC(=O)OR$^{312}$, —OC(=O)NR$^{312}$R$^{322}$, —OC(=O)SR$^{312}$, —SC(=O)OR$^{312}$, —SC(=)NR$^{312}$R$^{322}$, —P(O)OR$^{312}$OR$^{322}$, $C_{1-10}$alkylidene, $C_{0-10}$alkyl, $C_{2-10}$alkenyl, $C_{2-10}$alkynyl, —$C_{1-10}$alkoxy $C_{1-10}$alkyl, —$C_{1-10}$alkoxyC$_{2-10}$alkenyl, —$C_{1-10}$alkoxy $C_{2-10}$alkynyl, —$C_{1-10}$alkylthioC$_{1-10}$alkenyl, —$C_{1-10}$alkylthioC$_{2-10}$alkenyl, —$C_{1-10}$alkylthioC$_{2-10}$alkynyl, cyclo $C_{3-8}$alkyl, cycloC$_{3-8}$alkenyl, -cycloC$_{3-8}$alkylC$_{1-10}$alkyl, -cycloC$_{3-8}$alkenylC$_{1-10}$alkyl, -cycloC$_{3-8}$alkylC$_{2-10}$alkenyl, -cycloC$_{3-8}$alkenylC$_{2-10}$alkenyl, -cycloC$_{3-8}$alkylC$_{2-10}$alkynyl, -cycloC$_{3-8}$alkenylC$_{2-10}$alkynyl, -heterocyclyl-C$_{0-10}$alkyl, -heterocyclyl-C$_{2-10}$alkenyl, or -heterocyclyl-C$_{2-10}$alkynyl, any of which is optionally substituted with one or more independent halo, oxo, —CF$_3$, —OCF$_3$, —OR$^{313}$, —NR$^{313}$R$^{323}$, —C(O)R$^{323}$, —CO$_2$R$^{313}$, —C(=O)NR$^{313}$R$^{323}$, —NO$_2$, —CN, —S(O)$_{0-2}$R$^{313}$, —SO$_2$NR$^{313}$R$^{323}$, —NR$^{313}$C(=O) R$^{323}$, —NR$^{313}$C(=O)OR$^{323}$, —NR$^{313}$C(=O)NR$^{323}$R$^{333}$, —NR$^{313}$S(O)$_{0-2}$R$^{323}$, —C(=S)OR$^{313}$, —C(=O)SR$^{313}$, —NR$^{313}$C(=NR$^{323}$)NR$^{333}$R$^{342}$, —NR$^{313}$C(=NR$^{323}$) OR$^{333}$, —NR$^{313}$C(=NR$^{323}$)SR$^{333}$, —OC(=O)OR$^{333}$, —OC(=O)NR$^{313}$R$^{323}$, —OC(=O)SR$^{313}$, —SC(=O) OR$^{313}$, —P(O)OR$^{313}$OR$^{323}$, or —SC(=O)NR$^{313}$R$^{323}$ substituents;

or $G^{11}$ is aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —CF$_3$, —OCF$_3$, —OR$^{313}$, —NR$^{313}$R$^{323}$, —C(O)R$^{313}$, —CO$_2$R$^{313}$, —C(=O)NR$^{313}$R$^{323}$, —NO$_2$, —CN, —S(O)$_{0-2}$R$^{313}$, —SO$_2$NR$^{313}$R$^{323}$, —NR$^{313}$C(=O)R$^{323}$, —NR$^{313}$C(=O)OR$^{323}$, —NR$^{313}$C(=O)NR$^{323}$R$^{333}$, —NR$^{313}$S(O)$_{0-2}$R$^{323}$, —C(=S)OR$^{313}$, —C(=O)SR$^{313}$, —NR$^{323}$C(=NR$^{313}$)NR$^{333}$R$^{342}$, —NR$^{313}$C(=NR$^{323}$) OR$^{333}$, —NR$^{313}$C(=NR$^{323}$)SR$^{333}$, —OC(=O)OR$^{313}$, —OC(=O)NR$^{313}$R$^{323}$, —OC(=O)SR$^{313}$, —SC(=O) OR$^{313}$, —P(O)OR$^{313}$OR$^{323}$, or —SC(=O)NR$^{313}$R$^{323}$ substituents; provided that $G^{11}$ is not N—CH$_2$CO$_2$H when $R^3$ is 4-piperidinyl;

$R^{31}$, $R^{32}$, $R^{33}$, $R^{311}$, $R^{321}$, $R^{331}$, $R^{312}$, $R^{322}$, $R^{332}$, $R^{341}$, $R^{313}$, $R^{323}$, $R^{333}$, and $R^{342}$, in each instance, is independently:

$C_{0-8}$alkyl optionally substituted with an aryl, heterocyclyl or hetaryl substituent, or $C_{0-8}$alkyl optionally substituted with 1-6 independent halo, —CON($C_{0-8}$alkyl)($C_{0-8}$alkyl), —CO($C_{0-8}$alkyl), —O$C_{0-8}$alkyl, —Oaryl, —Ohetaryl, —Oheterocyclyl, —S(O)$_{0-2}$aryl, —S(O)$_{0-2}$hetaryl, —S(O)$_{0-2}$heterocyclyl, —S(O)$_{0-2}C_{0-8}$alkyl, —N($C_{0-8}$alkyl)($C_{0-8}$alkyl), —N($C_{0-8}$alkyl)CON($C_{0-8}$alkyl)($C_{0-8}$alkyl), —N($C_{0-8}$alkyl)CO($C_{1-8}$alkyl), —N($C_{0-8}$alkyl)CO($C_{3-8}$cycloalkyl), —N($C_{0-8}$alkyl)CO$_2$($C_{1-8}$alkyl), S(O)$_{1-2}$N($C_{0-8}$alkyl)($C_{0-8}$alkyl), —NR$^{11}$S(O)$_{1-2}$($C_{0-8}$alkyl), —CON($C_{3-8}$cycloalkyl)($C_{3-8}$cycloalkyl), —CON($C_{0-8}$alkyl)($C_{3-8}$cycloalkyl), —N($C_{3-8}$cycloalkyl)CON($C_{0-8}$alkyl)($C_{0-8}$alkyl), —N($C_{3-8}$cycloalkyl)CON($C_{3-8}$cycloalkyl)($C_{0-8}$alkyl), —N($C_{0-8}$alkyl)CON($C_{3-8}$cycloalkyl)($C_{0-8}$alkyl), —N($C_{0-8}$alkyl)CO$_2$($C_{3-8}$cycloalkyl), —N($C_{3-8}$cycloalkyl)CO$_2$($C_{3-8}$cycloalkyl), S(O)$_{1-2}$N($C_{0-8}$alkyl)($C_{3-8}$cycloalkyl), —NR$^{11}$S(O)$_{1-2}$($C_{3-8}$cycloalkyl), $C_{2-8}$alkenyl, $C_{2-8}$alkynyl, CN, CF$_3$, OH, or optionally substituted aryl substituents; such that each of the above aryl, heterocyclyl, hetaryl, alkyl or cycloalkyl groups may be optionally, independently substituted with —N($C_{0-8}$alkyl)($C_{0-8}$alkyl), hydroxyl, halogen, oxo, aryl, hetaryl, $C_{0-6}$alkyl, —$C_{0-8}$alkylcyclyl, —$C_{0-8}$alkyl-N($C_{0-8}$alkyl)-S(O)$_{0-2}$—($C_{0-8}$alkyl), —$C_{0-8}$alkyl-S(O)$_{0-2}$—N($C_{0-8}$alkyl)($C_{0-8}$alkyl), —$C_{0-8}$alkyl-N($C_{0-8}$alkyl)CO($C_{0-8}$alkyl), —$C_{0-8}$alkyl-N($C_{0-8}$alkyl)CO—N($C_{0-8}$alkyl)($C_{0-8}$alkyl), —$C_{0-8}$alkyl-CO—N($C_{0-8}$alkyl)($C_{0-8}$alkyl), —$C_{1-8}$alkyl-CO$_2$—($C_{0-8}$alkyl), —$C_{0-8}$alkylS(O)$_{0-2}$—($C_{0-8}$alkyl), —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocyclyl, —$C_{0-8}$alkyl-O—$C_{0-8}$alkylaryl, —$C_{0-8}$alkyl-O—$C_{0-8}$alkylhetaryl, —$C_{0-8}$alkyl-S—$C_{0-8}$alkylcyclyl, —$C_{0-8}$alkyl-S—$C_{0-8}$alkylcyclyl, —$C_{0-8}$alkyl-S—$C_{0-8}$alkylheterocyclyl, —$C_{0-8}$alkyl-S—$C_{0-8}$alkylaryl, —$C_{0-8}$alkyl-S—$C_{0-8}$alkylhetaryl, —$C_{0-8}$alkyl-N($C_{0-8}$alkyl)-$C_{0-8}$alkyl, —$C_{0-8}$alkyl-N($C_{0-8}$alkyl)-$C_{0-8}$alkylcyclyl, —$C_{0-8}$alkyl-N($C_{0-8}$alkyl)-$C_{0-8}$alkylheterocyclyl, —$C_{0-8}$alkyl-N($C_{0-8}$alkyl)-$C_{0-8}$alkylaryl, —$C_{0-8}$alkyl-N($C_{0-8}$alkyl)-$C_{0-8}$alkylhetaryl, —$C_{2-8}$alkenyl, —$C_{2-8}$alkynyl, NO$_2$, CN, CF$_3$, OCF$_3$, OCHF$_2$, —$C_{0-8}$alkyl-$C_{3-8}$cycloalkyl, —$C_{0-8}$alkyl-O—$C_{0-8}$alkyl, —$C_{0-8}$alkyl-N($C_{0-8}$alkyl)($C_{0-8}$alkyl), —$C_{0-8}$alkyl-S(O)$_{0-2}$—$C_{0-8}$alkyl, or heterocyclyl optionally substituted with 1-4 independent $C_{0-8}$alkyl, cyclyl, or substituted cyclyl substituents;

$E^1$ in each instance is independently halo, —CF$_3$, —OCF$_3$, —OR$^2$, —NR$^{31}$R$^{32}$, —C(=O)R$^{31}$, —CO$_2$R$^{31}$, —CONR$^{31}$R$^{32}$, —NO$_2$, —CN, —S(O)$_{0-2}$R$^{31}$, —S(O)$_{0-2}$NR$^{31}$R$^{32}$, —NR$^{31}$C(=O)$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{31}$)SR$^{31}$, —OC(=O)OR$^{31}$, —OC(=O)NR$^{31}$R$^{32}$, —OC(=O)SR$^{31}$, —SC(=O)OR$^{31}$, —SC(=O)NR$^{31}$R$^{32}$, $C_{0-10}$alkyl, $C_{2-10}$alkenyl, $C_{2-10}$alkynyl, —$C_{1-10}$alkoxy$C_{1-10}$alkyl, —$C_{1-10}$alkoxy$C_{2-10}$alkenyl, —$C_{1-10}$alkoxy$C_{2-10}$alkynyl, —$C_{1-10}$-alkylthio$C_{1-10}$alkyl, —$C_{1-10}$alkylthio$C_{2-10}$alkenyl, —$C_{1-10}$alkylthio$C_{2-10}$alkynyl, cyclo$C_{3-8}$alkyl, cyclo$C_{3-8}$alkenyl, -cyclo$C_{3-8}$alkyl$C_{1-10}$alkyl, -cyclo$C_{3-8}$alkenyl$C_{1-10}$alkyl, -cyclo$C_{3-8}$alkyl$C_{2-10}$alkenyl, -cyclo$C_{3-8}$alkenyl$C_{2-10}$alkenyl, -cyclo$C_{3-8}$alkyl$C_{2-10}$alkynyl, -cyclo$C_{3-8}$alkenyl$C_{2-10}$alkynyl, -heterocyclyl-$C_{0-10}$alkyl, -heterocyclyl-$C_{2-10}$alkenyl, or -heterocyclyl-$C_{2-10}$alkynyl, any of which is optionally substituted with one or more independent halo, oxo, —CF$_3$, —OCF$_3$, —OR$^{31}$, —NR$^{31}$R$^{32}$, —C(=O)R$^{31}$, —CO$_2$R$^{31}$, —C(=O)NR$^{31}$R$^{32}$, —NO$_2$, —CN, —S(=O)$_{0-2}$R$^{31}$, —SO$_2$NR$^{31}$, —NR$^{31}$C(=O)$^{32}$, —NR$^{31}$C(=O)OR$^{31}$, —NR$^{31}$C(=O)NR$^{32}$R$^{33}$, —NR$^{31}$S(O)$_{0-2}$R$^{31}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

or $E^1$ in each instance is independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —CF$_3$, —OCF$_3$, —OR$^{31}$, —NR$^{31}$R$^{32}$, —C(O)R$^{31}$, —CO$_2$R$^{31}$, —C(=O)NR$^{31}$R$^{32}$, —NO$_2$, —CN, —S(O)$_{0-2}$R$^{31}$, —S(O)$_{0-2}$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

in the cases of —NR$^{31}$R$^{32}$, —NR$^{311}$R$^{321}$, —NR$^{312}$R$^{322}$, —NR$^{332}$R$^{341}$, —NR$^{313}$R$^{323}$, and —NR$^{323}$R$^{333}$, the respective R$^{31}$ and R$^{32}$, R$^{311}$ and R$^{321}$, R$^{312}$ and R$^{322}$, R$^{331}$ and R$^{341}$, R$^{313}$ and R$^{323}$, and R$^{323}$ and R$^{333}$ are optionally taken together with the nitrogen atom to which they are attached to form a 3-10 membered saturated or unsaturated ring; wherein said ring in each instance independently is optionally substituted by one or more independent —N($C_{0-8}$alkyl)($C_{0-8}$alkyl), hydroxyl, halogen, oxo, aryl, hetaryl, $C_{0-6}$alkyl, —$C_{0-8}$alkyl$C_{3-8}$cycloalkyl, —$C_{0-8}$alkyl-N($C_{0-8}$alkyl)S(O)$_{0-2}C_{0-8}$alkyl, —$C_{0-8}$alkyl-N($C_{0-8}$alkyl)S(O)$_{0-2}$N($C_{0-8}$alkyl)($C_{0-8}$alkyl), —$C_{0-8}$alkyl-N($C_{0-8}$alkyl)CO$_2$($C_{0-8}$alkyl), —$C_{0-8}$alkyl-CON(($C_{0-8}$alkyl))S(O)$_{0-2}$($C_{0-8}$alkyl), —$C_{0-8}$alkyl-S(O)$_{0-2}$N($C_{0-8}$alkyl)($C_{0-8}$alkyl), —$C_{0-8}$alkyl-N($C_{0-8}$alkyl)(CO($C_{0-8}$alkyl), —CO$_{0-8}$alkyl-N($C_{0-8}$alkyl)CON($C_{0-8}$alkyl)($C_{0-8}$alkyl), —$C_{0-8}$alkyl-CON($C_{0-8}$alkyl)($C_{0-8}$alkyl), —$C_{0-8}$alkyl-CO$_2$($C_{0-8}$alkyl), —$C_{0-8}$alkylS(O)$_{0-2}$($C_{0-8}$alkyl), —$C_{0-8}$alkyl-O—$C_{0-8}$alkyl, —$C_{0-8}$alkyl-O—$C_{0-8}$alkylcyclyl, —$C_{0-8}$alkyl-O—$C_{0-8}$alkylheterocycloalkyl, —$C_{0-8}$alkyl-O—$C_{0-8}$alkylaryl, —Oaryl, $C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkyaryl, —$C_{0-8}$alkyl-S—$C_{0-8}$alkylhetaryl, —$C_{0-8}$alkyl-N($C_{0-8}$alkyl)-$C_{0-8}$alkyl, —$C_{0-8}$alkyl-N($C_{0-8}$alkyl)-$C_{0-8}$alkyl$C_{3-8}$cycloalkyl, —$C_{0-8}$alkyl-N($C_{0-8}$alkyl)-$C_{0-8}$alkylheterocycloalkyl, —$C_{0-8}$alkyl-N($C_{0-8}$alkyl)-$C_{0-8}$alkylaryl, —$C_{0-8}$alkyl-N($C_{0-8}$alkyl)-$C_{0-8}$alkylhetaryl, —$C_{0-8}$alkyl-N($C_{0-8}$alkyl)($C_{0-8}$alkyl), $C_{2-8}$alkenyl, $C_{2-8}$alkynyl, NO$_2$, CN, CF$_3$, OCF$_3$, or OCHF$_2$ substituents; wherein said ring in each instance independently optionally includes one or more heteroatoms other than the nitrogen; and m is 0, 1, 2, or 3; n is 0, 1, 2, 3, or 4; and aa is 0 or 1.

In some embodiments, the compound is not trans-4-[8-amino-1-(7-chloro-4-hydroxy-1H-indol-2-yl)imidazo[1,5-a]pyrazin-3-yl]cyclohexanecarboxylic acid, cis-3-[8-amino-1-(7-chloro-1H-indol-2-yl)imidazo[1,5-a]pyrazin-3-yl]cyclobutanecarboxylic acid, trans-4-{8-amino-1-[7-(3-isopropyl)phenyl-1H-indol-2-yl]imidazo[1,5-a]pyrazin-3-yl}cyclohexanecarboxylic acid, or trans-4-{8-amino-1-[7-(2,5-dichloro)phenyl-1H-indol-2-yl]imidazo[1,5-a]pyrazin-3-yl}cyclohexane carboxylic acid.

In some embodiments, there is provided a pharmaceutically acceptable salt selected from the group consisting of tromethamine, sodium, calcium and L-arginine of a compound selected from the following:

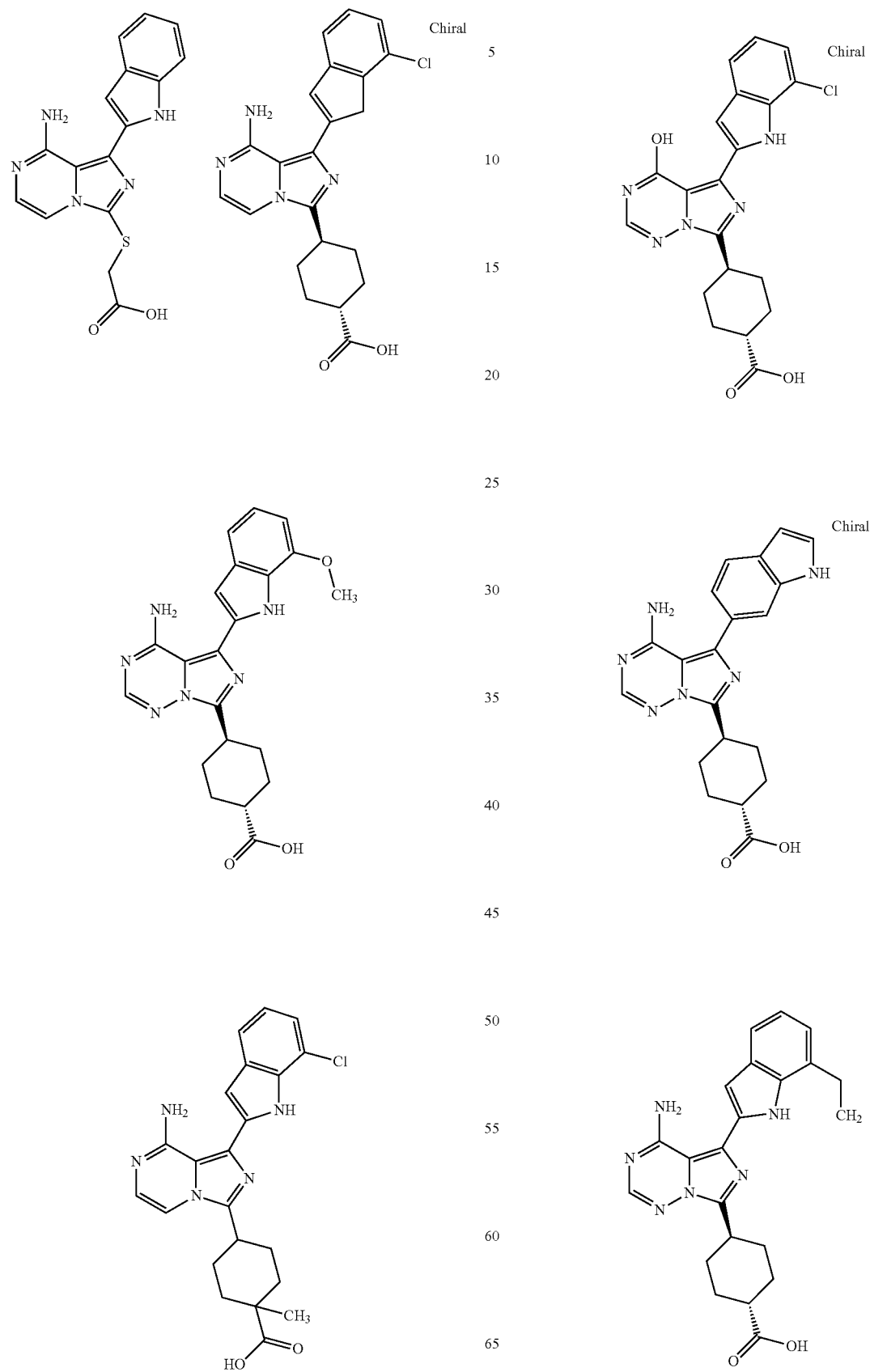

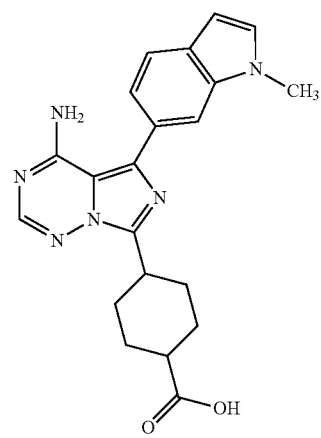
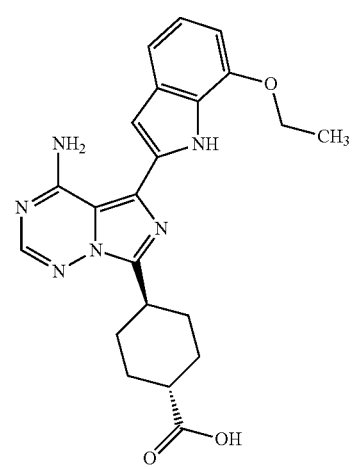
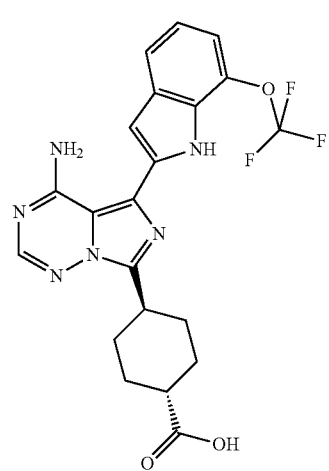
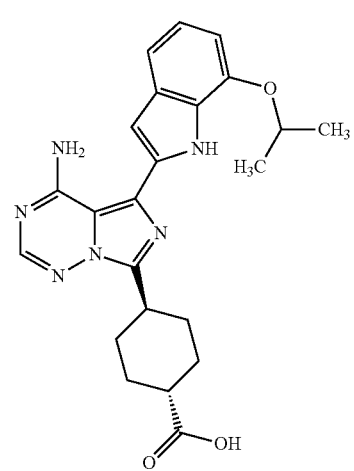
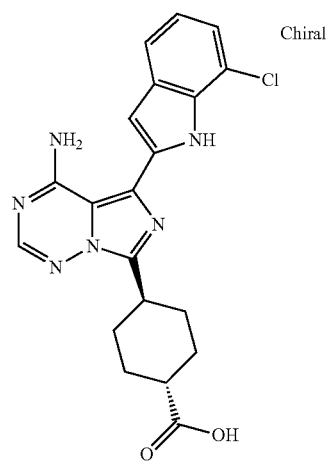
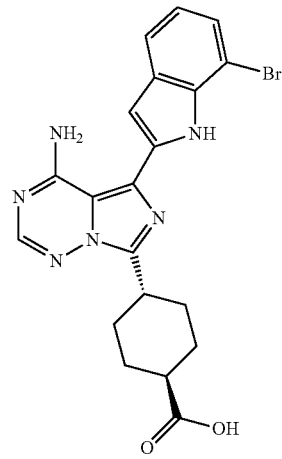

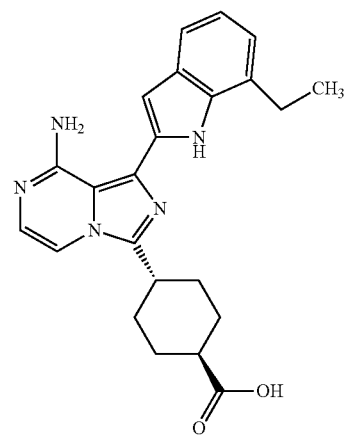
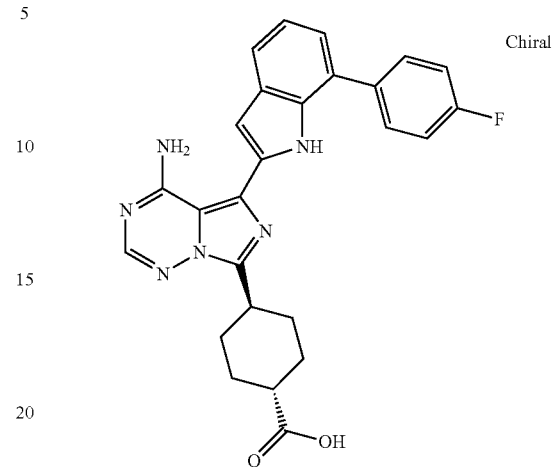
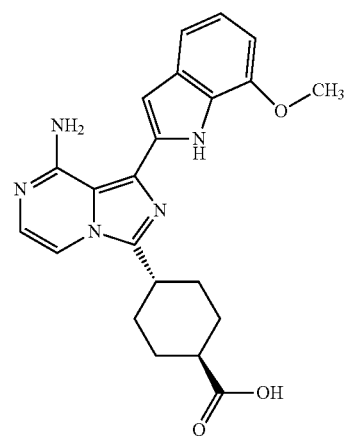
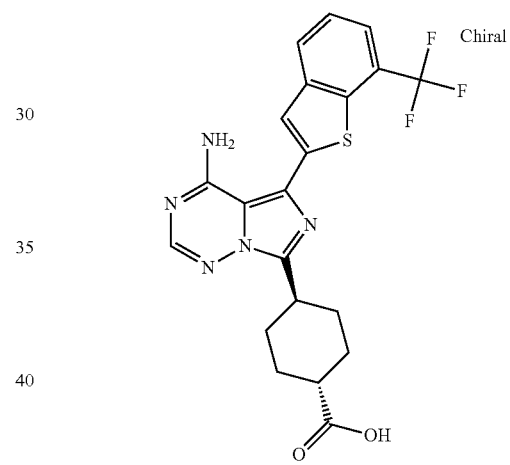
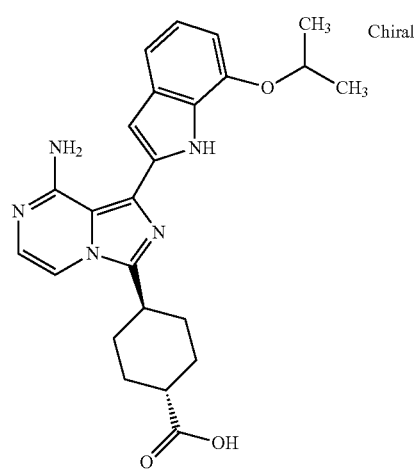
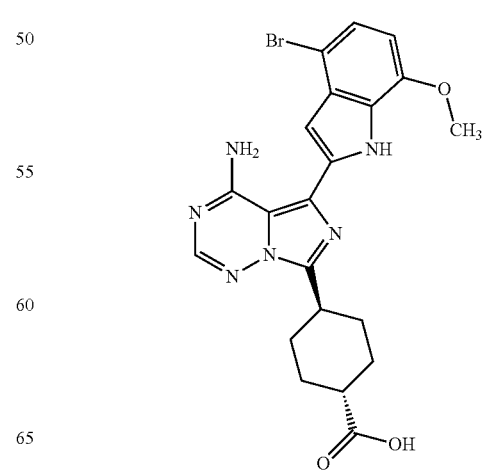

13
-continued
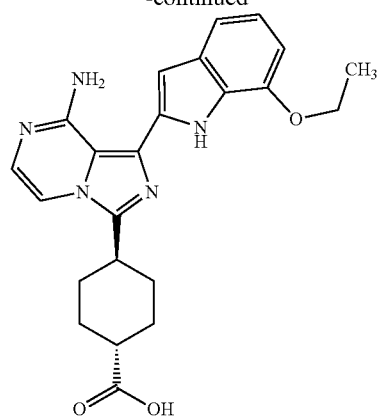
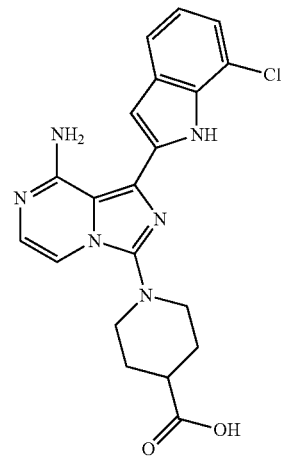
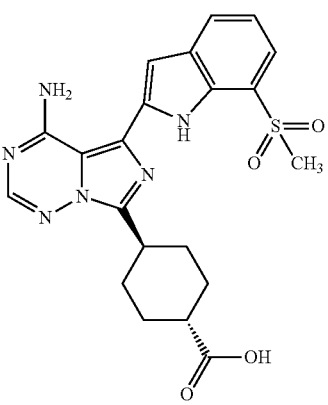
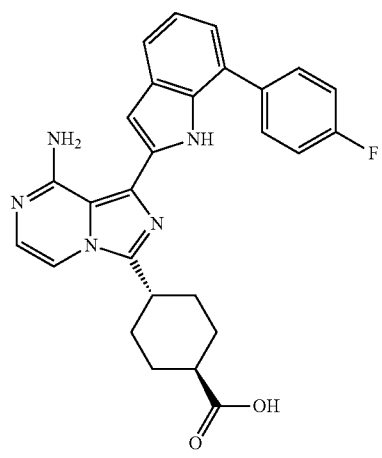
14
-continued
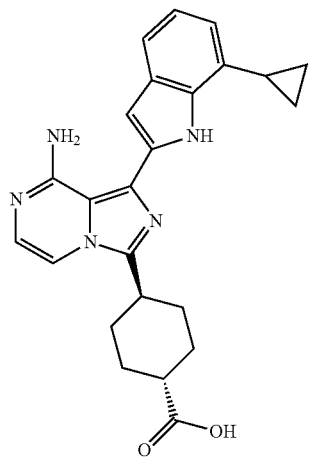
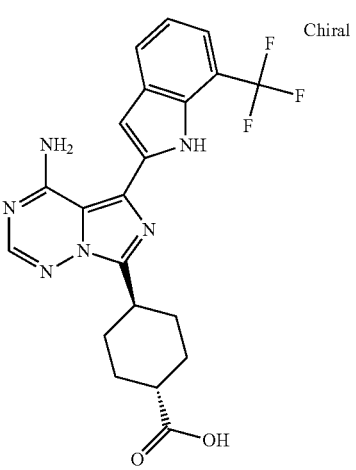
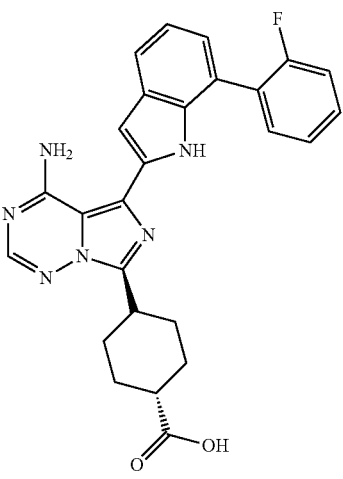

15
-continued
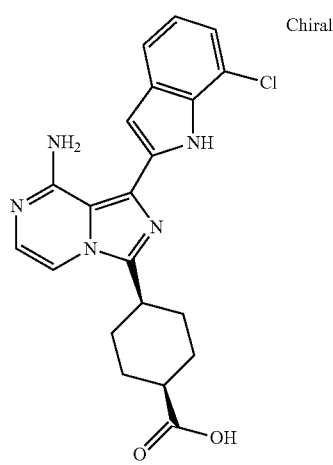
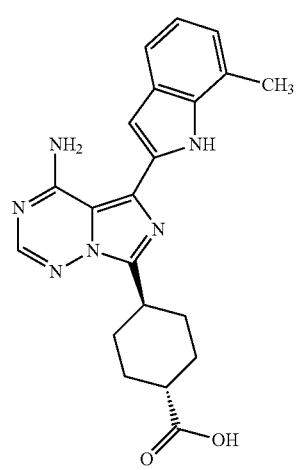
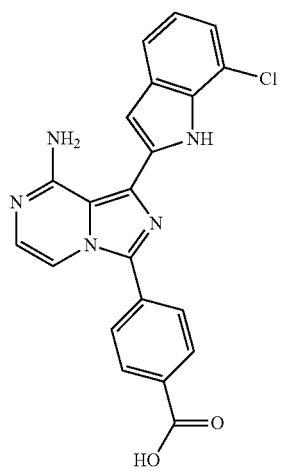
16
-continued
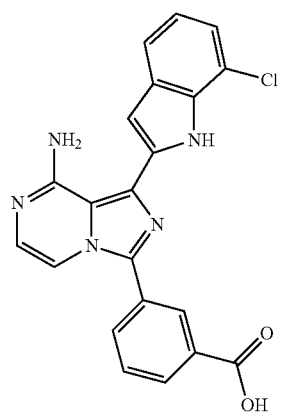
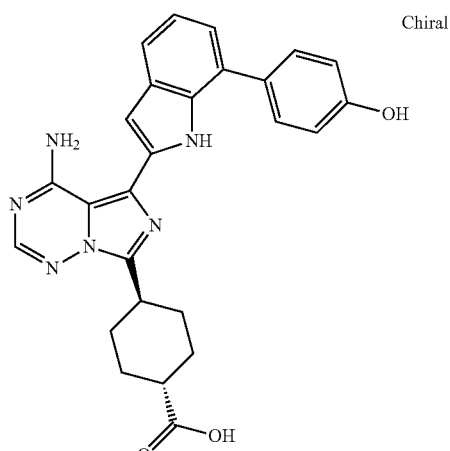
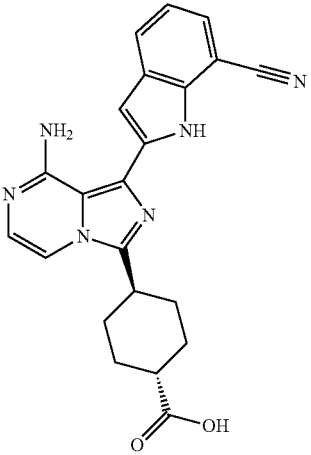

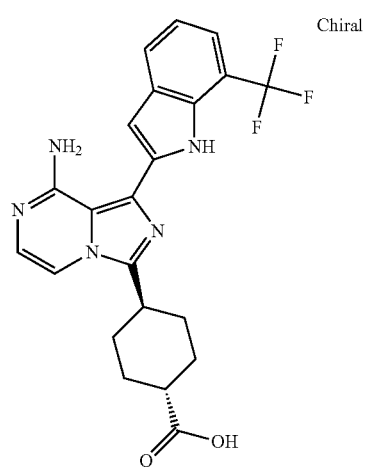
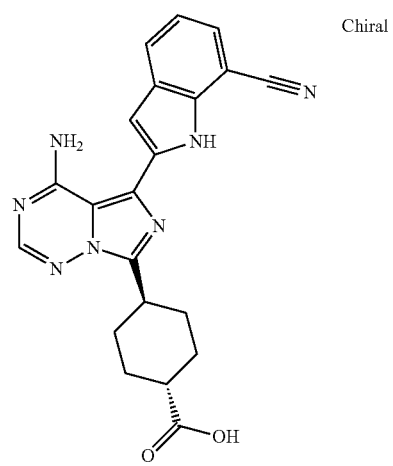
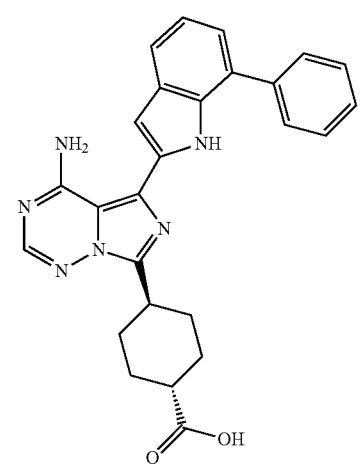
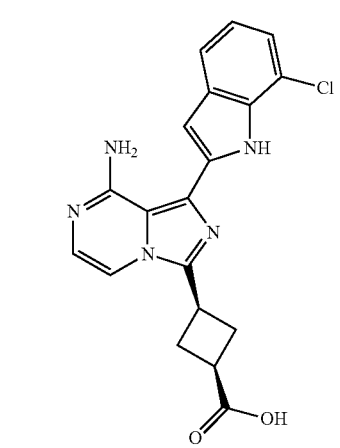
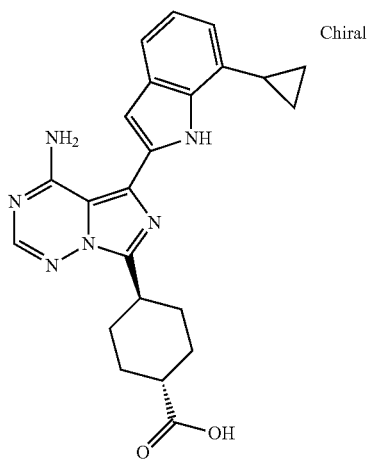
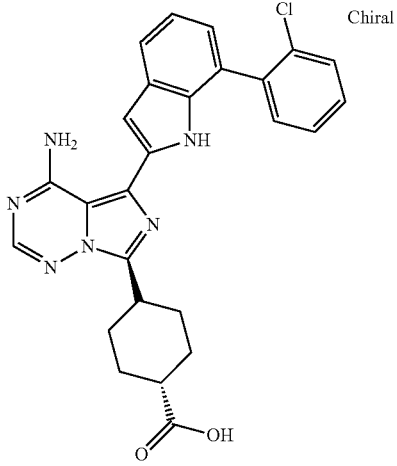

-continued
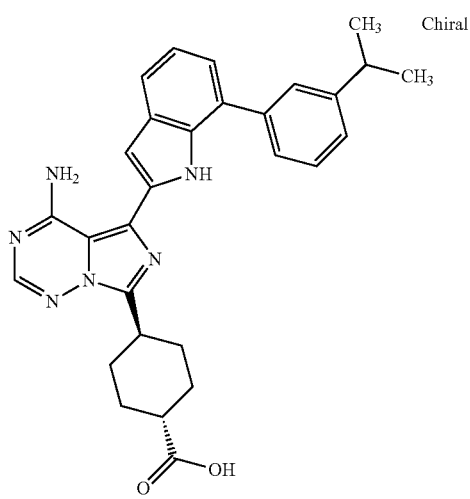
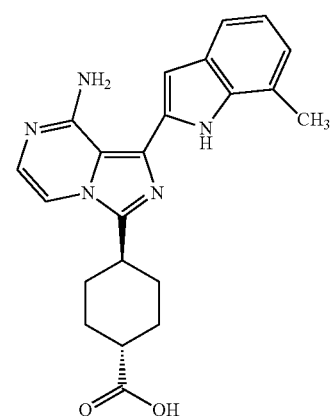
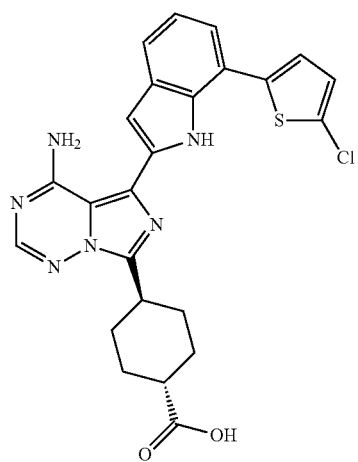
-continued
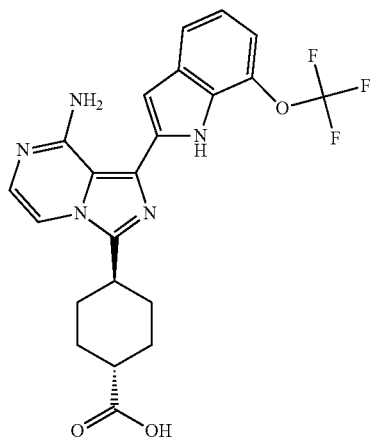
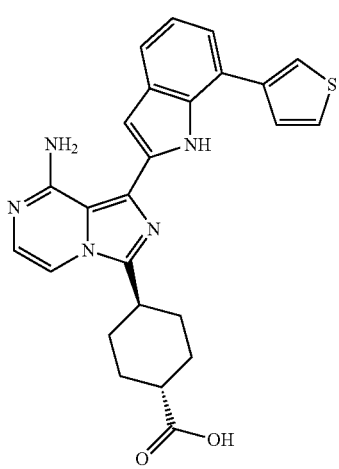
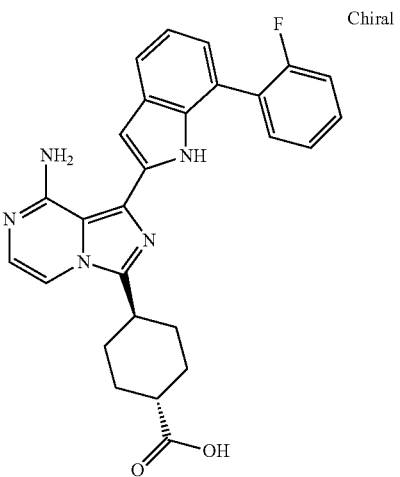

-continued
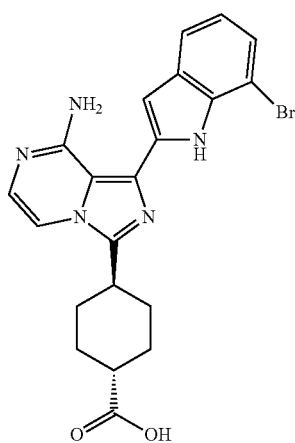
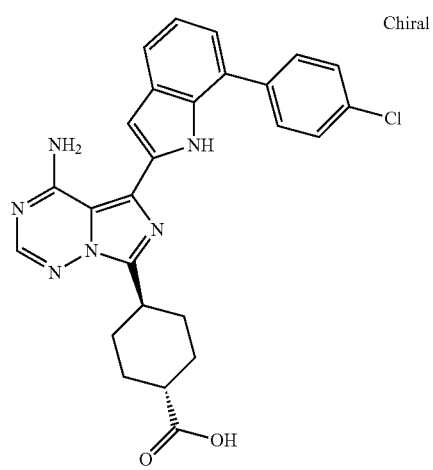
Chiral
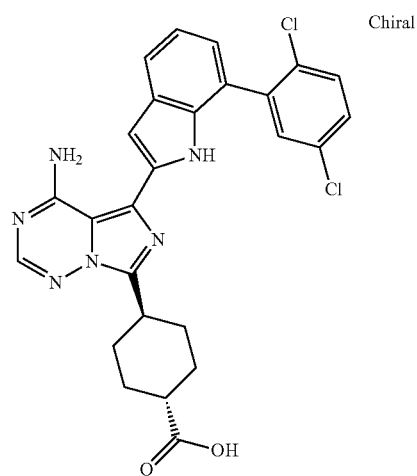
Chiral
-continued
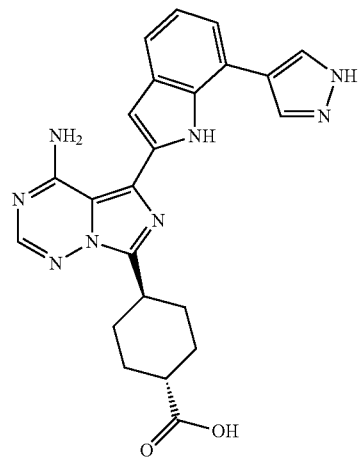
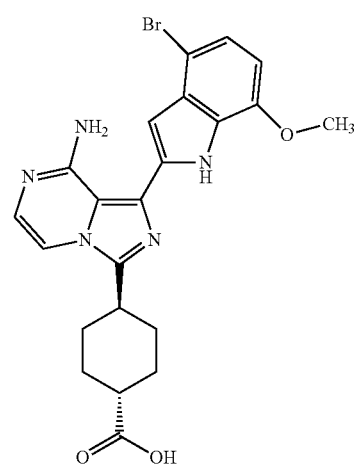
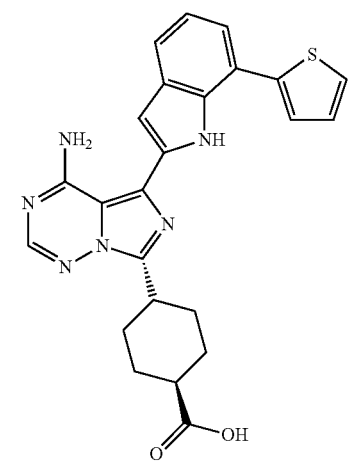

23
-continued
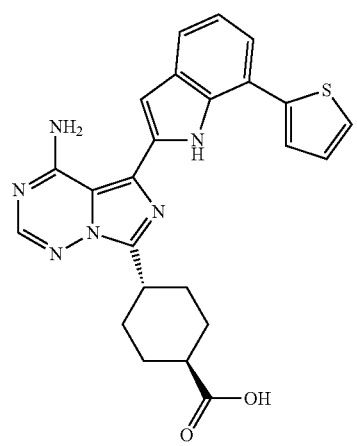
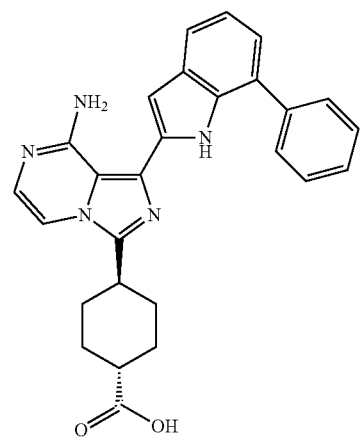
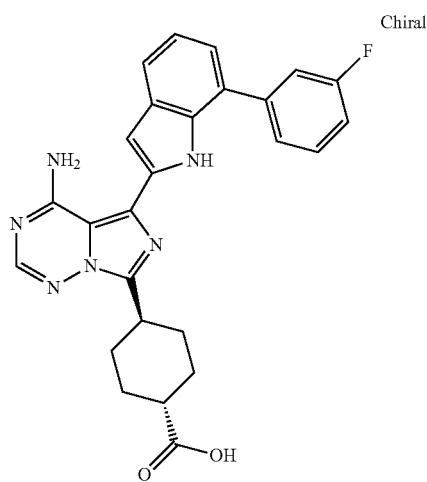
24
-continued
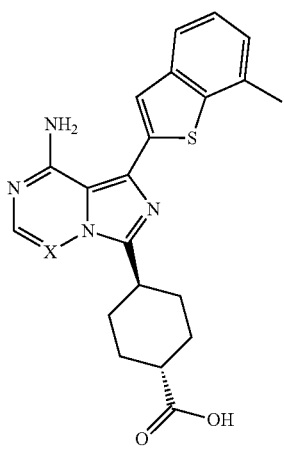
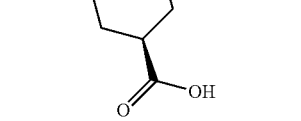
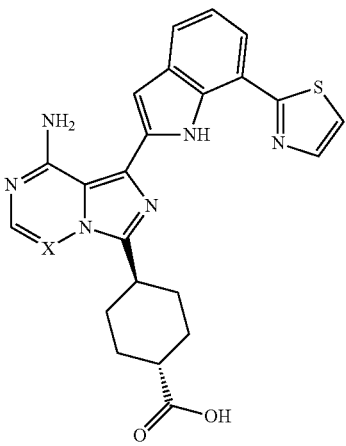

-continued

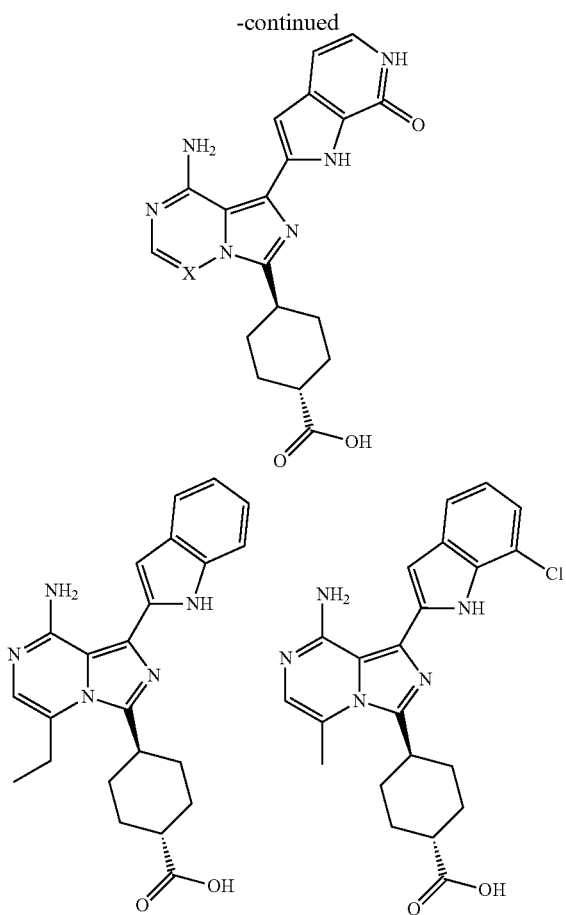

The compounds can be prepared according to the general skill in the art such as described in US2007/0112005.

In some embodiments, the salt is selected from tromethamine, sodium, calcium, or L-arginine. In some embodiments, the salt is selected from magnesium, potassium, N,N-diethylethanolamine, N-methyl-D-glucamine, or piperazine.

In some embodiments, there is provided a pharmaceutically acceptable salt of trans-4-[4-amino-5-(7-methoxy-1H-indol-2-yl)imidazo[5,1-f][1,2,4]triazin-7-yl]cyclohexane carboxylic acid, wherein the salt is selected from sodium, calcium, L-arginine, magnesium, potassium, N,N-diethylethanolamine, N-methyl-D-glucamine, or tromethamine.

In some embodiments, the salt form is selected from sodium, calcium, or L-arginine. In some embodiments, the salt form is selected from magnesium, potassium, N,N-diethylethanolamine, or N-methyl-D-glucamine. In some embodiments, the salt form is tromethamine.

In some embodiments, the salt, form is a hydrate or solvate salt form. In some embodiments, the salt form is substantially amorphous. In some embodiments, the salt form is substantially crystalline.

In some embodiments, the salt form is at least about 95% by weight crystalline. In some embodiments, the salt form is substantially a single crystalline form.

In some embodiments, the salt form degrades by about 1% by weight or less during 30 days at 40° C. and 75% RH.

In some embodiments, the salt form is a tromethamine salt that exhibits an X-ray powder diffraction pattern substantially resembling that of FIG. 1. In some embodiments, the salt form is a tromethamine form, which exhibits an endotherm at a temperature of about 202-211° C. via DSC analysis. In some embodiments, the salt form is a tromethamine form which has a solubility in water of about 6 mg/mL. In some embodiments, the salt form is a tromethamine form having a $^{13}$C NMR spectrum substantially similar to that of Example 1. In some embodiments, the salt form is a tromethamine form having a hygroscopicity of 2-4% at 90-95% RH.

In some embodiments, the salt form is prepared by reacting (tromethamine) 1,3-propanediol, 2-amino-2-(hydroxymethyl) (about 1-2 eq) in MeOH at reflux for about 1 h, cooling, filtering, washing, and drying. In some embodiments, the starting free compound is initially free of inorganic salts. Crystallization of the free compound from EtOH or EtOH/water can be particularly useful in removing residual Pd if present. In some embodiments, the tromethamine salt is formed by reaction with about 3 eq tromethamine in EtOH or EtOH:water 1:1. In some embodiments, the tromethamine salt is prepared in MeOH:THF and slow cooled.

Figure 2:
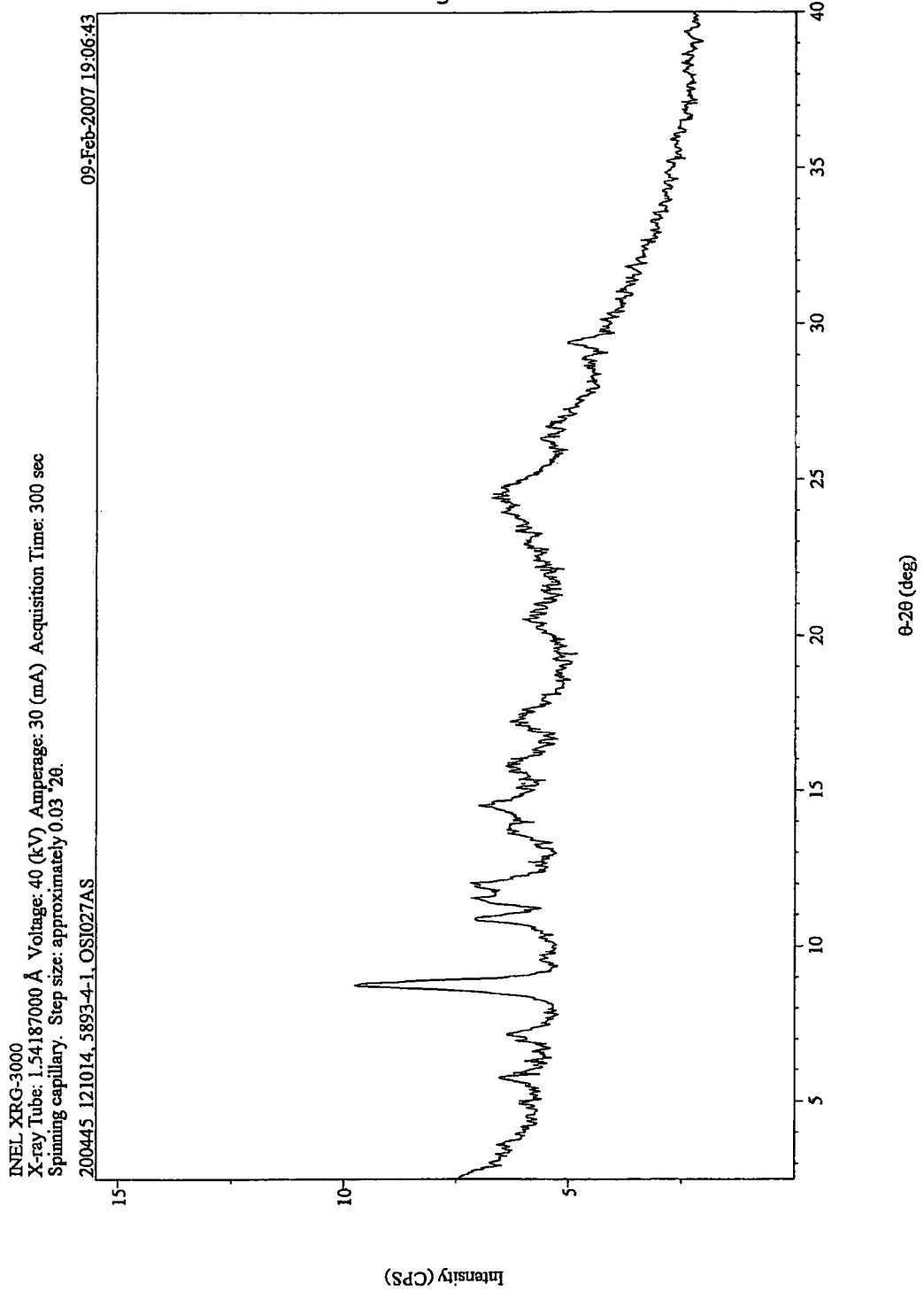
FIG. 2: XRPD pattern of Example 2 calcium salt form.

In some embodiments, the salt form is a calcium salt that exhibits an X-ray powder diffraction pattern substantially resembling that of FIG. 2.

Biological Activity: Inhibition of mTOR Activity

The ability of compounds to inhibit the mTOR kinase activity was determined in an in vitro immunoprecipitation (IP) kinase assay using recombinant 4E-BP1 as a substrate. The assay determines the ability of compounds to inhibit phosphorylation of 4E-BP1 a well-known physiological substrate of mTOR. The immunocapture mTOR complex from HeLa cells is incubated with various concentrations of compounds and His-tag 4E-BP1 in kinase assay buffer prior to addition of ATP to start the reaction at RT. The reaction is stopped after 30 minutes and the phosphorylated His-tag 4E-BP1 is captured on a Nickel-chelate plate overnight at 4° C. The phosphothreonine content of 4E-BP1 is then measured using phospho-4E-BP1 (T37/46) primary antibody and corresponding anti rabbit IgG HRP conjugated, secondary antibody. The secondary antibody has a reporter enzyme (e.g. horseradish peroxidase, HRP) covalently attached, such that binding of primary antibody to phosphorylated 4E-BP1 can be determined quantitatively which is equal to the amount of secondary antibody bound to it. The amount of secondary antibody can be determined by incubation with an appropriate IMP substrate.

The stock reagents used are as follows: Cell lysis buffer: 40 mM HEPES, pH 7.5 containing 120 mM NaCl, 1 mM EDTA, 10 mM sodium pyrophosphate, 10 mM (3-glycerophosphate, 50 mM sodium fluoride, 1.5 mM sodium vanadate and 0.3% CHAPS. Complete mini EDTA-free protease inhibitors (Roche, catalog #11 836 170 001). HeLa cell pellets (Paragon Bioservices). Protein G coated plates for immunoprecipitation (Pierce, catalog #15131). mTOR (aka FRAP) N-19 antibody (Santa Cruz Biotechnology, catalog #sc-1549). IP Wash Buffer: 50 mM HEPES, pH 7.5 containing 150 mM NaCl. Kinase Buffer: 20 mM HEPES, pH 7.5 containing 10 mM MgCl2, 4 mM MnCl2, 10 mM b-mercaptoethanol and 200 uM sodium vanadate. Make fresh for assay. Recombinant 4E-BP1 (aka PHAS I) (Calbiochem, catalog #516675). Dilute 4E-BP1 stock (1 mg/mL) 120 times in kinase assay buffer to obtain a concentration of 0.25 µg/well in 30 uL. ATP Solution Prepare 330 uM ATP stock in kinase buffer. Ni-chelate Plate (Pierce, catalog #15242). Antibody Dilution Buffer: TBST containing 5% skim milk. Phospho-4E-BP1 (T37/46) Antibody: 1:1000 dilution of phospho-4E-BP1 (T37/46) antibody (Cell Signaling Technology, catalog #9459) in antibody dilution buffer. Donkey anti rabbit IgG, HRP conjugated 1:10,000 dilution of anti rabbit IgG HRP conjugated (GE Healthcare, Catalog# NA934) in antibody dilution buffer. HRP substrate: Chemiluminescent reagents (Pierce, catalog# 37074)

Assay Protocol: HeLa cell lysate was prepared in bulk by homogenizing 25 g of cell pellet in 60 mL of cell lysis buffer and then, centrifuged, at 12,000 rpm for 30 min. The clear supernatant was transferred to a fresh tube, aliquoted, quickly frozen and stored at −80° C. until use. Protein G coated 96-well plate is washed once with lysis buffer and 50 µL of diluted mTOR antibody is added to each well, and incubated at RT for 30-60 min. Then, 50 µg of HeLa cell lysate was added to each well in 50 µL of lysis buffer and incubated at 4° C. in a cold room on a shaker for 2-3 h. Lysate was removed and the plate was washed with 100 µL of complete lysis buffer (3 times). The plate was further washed 2 times with 100 µL of high salt wash buffer. Diluted 4E-BP1 (substrate) is added to each well in 30 µL. The compounds were added in various concentrations in 5 µL to each well. The drug concentrations varied from 30 µM to 0.1 µM. The final DMSO concentration was 1%. Only DMSO was added to positive control wells. For negative control wells, no ATP solution was added but instead 15 µL of kinase buffer was added, the reaction was started by addition of ATP in 15 µL to a final concentration of 100 µM to the rest of the wells except negative control wells. The reaction was carried out for 30 min at RT. Then, 45 µL of the reaction mixture was transferred to Ni-chelate plate and incubated overnight at 4° C. The plate was washed once with antibody dilution buffer and 50 µL of diluted phospho-4E-BP1 antibody was added to each well, and incubated at RT for 1 h. Then, the plate was washed with TBST (4 times) and 50 µL of diluted anti-rabbit secondary antibody was added to each plate, and incubated at RT for 1 h. The plate was washed with 100 µL of TBST (4 times). To each well, 50 µL of Pierce Femto chemiluminescent reagent was added and the chemiluminescence was measured using a victor machine.

Comparison of the assay signals obtained in the presence of compound with those of positive and negative controls, allows the degree of inhibition of phospho-4E-BP1 phosphorylation to be determined over a range of compound concentrations. These inhibition values were fitted to a sigmoidal dose-response inhibition curve to determine the $IC_{50}$ values (i.e. the concentration of the compound that inhibits phosphorylation of 4E-BP1 by 50%).

mTOR Cell-based Mechanistic Assay to Measure the Inhibition of Phosphorylation of 4E-BP1 (T37/46)

MDA-MB-231 cells were plated in 96 well plates at $2 \times 10^4$ cells/well in 90 uL of Complete growth medium and incubated at 37° C. overnight in a $CO_2$ incubator. Cells were treated with various compounds in a dose response manner for 3 h at 37° C. in a $CO_2$ incubator before making cell lysates to measure inhibition of phosphorylation of 4E-BP1 at T37/46. Cell lysates' were transferred to a 96-well plate coated with 4E-BP1 antibodies to capture phospho-4E-BP1 (T37/46) and incubated overnight at 4° C. The amount of phospho-4E-BP1 in each well is further measured by incubating the wells with anti-rabbit phospho-4E-BP1 (T37/46) antibodies and a corresponding goat anti-rabbit IgG conjugated to HRP. The amount of HRP present in each well is measured by a chemiluminescence method, which corresponds to amount of phospho-4E-BP1 in each well. $IC_{50}$ values were determined using a 6-point dose response curve.

Compounds of this invention demonstrated at least one of the following: I) Inhibited phosphorylation of 4E-BP1 by immunocaptured human mTOR as determined in the biochemical assay for Inhibition of mTOR Activity with $IC_{50}$ values between 0.001 µM and 11.00 µM. It is advantageous that the $IC_{50}$ values be less than 1.00 µM and more advantageous that the $IC_{50}$ values be below 0.1 µM. Even more advantageous, the $IC_{50}$ values be less than 0.01 µM; II) Inhibited the phosphorylation of 4E-BP1 (T37/46) in the mTOR Cell-based Mechanistic Assay with $IC_{50}$ values below 40 µM. For example, trans-4-[4-amino-5-(7-methoxy-1H-indol-2-yl)-imidazo[5,1-f][1,2,4]triazin-7-yl]cyclohexanecarboxylic acid inhibited the phosphorylation of 4E-BP1 (T37/46) in the mTOR cell-based mechanistic assay with an $IC_{50}$ value of about 1 µM.

Pharmaceutical Compositions

The present invention includes compositions comprising a compound salt of the invention formulated for a desired mode of administration, with or without one or more pharmaceutically acceptable carriers or excipients.

The pharmaceutical compositions of the present invention comprise at least one compound as an active ingredient, optionally a pharmaceutically acceptable carrier and optionally other adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder; lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material, which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms. Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, EtOH, polyol (e.g., glycerol, propylene glycol and liquid polyethylene glycol), vegetable oils, and suitable mixtures thereof.

In addition to the aforementioned carrier ingredients, the pharmaceutical formulations described above may include, as appropriate, one, or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a salt of the invention may also be prepared in powder or liquid concentrate form.

The present invention includes a composition comprising a compound salt of the invention and at least one additional active agent, such as additional anti-neoplastic, anti-tumor, anti-angiogenic, or chemotherapeutic agent(s).

Methods of Treatment

The present invention includes a method of treatment of hyperproliferative disorders, including cancer, comprising administering to a patient in need thereof an effective amount of a compound salt of the invention. The disorder can be ovarian cancer, lymphoma, breast cancer, lung cancer, non-small cell lung cancer, kidney cancer, renal cell carcinoma, prostate cancer, cancer of the blood, liver cancer, ovarian cancer, thyroid cancer, endometrial cancer, cancer of the GI tract, renal cell carcinoma, mantle cell lymphoma, or endometrial cancer.

Thus, there is provided a method of treating a tumor comprising administering to a patient in need thereof an effective amount of a compound salt of the present invention. In some embodiments thereof, the cancer is lymphoma or ovarian cancer.

Generally, dosage levels of about 0.01 mg/kg to about 150 mg/kg of body weight per day may be useful in the treatment of the above-indicated conditions, or alternatively about 0.5 mg to about 7 g per patient per day. For example, cancers of the breast, lung, kidney, prostate, blood, liver, ovarian, thyroid, GI tract and lymphoma may be effectively treated by the administration of from about 0.01 to 50 mg of the compound per kilogram of body weight per day, or alternatively about 0.5 mg to about 3.5 g per patient per day. In some embodiments, about 0.05 mg to about 2 mg per patient per day may be administered, or about 0.1 mg to about 1 mg/kg. The actual dosing for any particular patient will depend upon a variety of factors including the age, body weight, general health, sex, diet, time of administration, route of administration, rate of excretion, drug combination and the severity of the particular disease undergoing therapy.

EXAMPLES

The compound trans-4-[4-amino-5-(7-methoxy-1H-indol-2-yl)-imidazo[5,1-f][1,2,4]triazin-7-yl]-cyclohexanecarboxylic acid is known and can be prepared according to US 2007/0112005 (Example 258 thereof). Salts of trans-4-[4-amino-5-(7-methoxy-1H-indol-2-yl)imidazo[5,1f][1,2,4]triazin-7-yl]cyclohexane carboxylic acid, including its calcium, magnesium, potassium, sodium, L-arginine, N-methyl-D-glucamine, piperazine, and tromethamine salts were prepared.

Example 1 trans-4-[4-amino-5-(7-methoxy-1H-indol-2-yl)imidazo[5,1-f][1,2,4]triazin-7-yl]cyclohexane carboxylic acid tromethamine salt

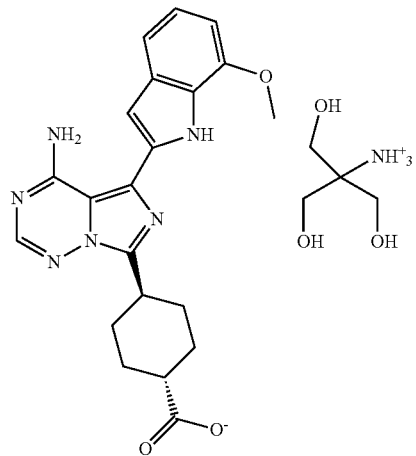

The compound trans-4-[4-Amino-5-(7-methoxy-1H-indol-2-yl)-imidazo[5,1-f][1,2,4]triazin-7-yl]-cyclohexanecarboxylic acid can be prepared as known in the art, e.g., according to US 2007/0112005 (Example 258 thereof). This product (5.01 g, 12.3 mmol) was suspended in MeOH (75.0 mL) and heated to reflux. 1,3-Propanediol, 2-amino-2-(hydroxymethyl) (1.79 g, 14.8 mmol) was added and the reaction was heated at reflux for 1 h. The suspension was allowed to cool to RT and then filtered. The solid was washed with MeOH and then dried in vacuo overnight at 50° C. to provide the title compound as a tan solid (4.57 g, 70.2% yield). $^1$H NMR (400 MHz, CD$_3$OD): δ 1.67 (dddd, J=12.8, 12.8, 12.8, 2.8 Hz, 2H), 1.87 (dddd, J=13.2, 13.2, 13.2, 3.2 Hz, 2H), 2.14-2.17 (m, 4H), 234 (tt, J=12.4, 2.8 Hz, 1H), 3.40 (tt, J=12.4, 3.2 Hz, 1H), 3.65 (s, 6H), 4.01 (s, 3H), 6.75 (d, J=7.2 Hz, 1H), 6.75 (s, 1H), 7.04 (dd, J=7.6, 7.6 Hz, 1H), 7.23 (d, J=7.6 Hz, 1H), 7.88 (s, 1H). $^{13}$C NMR (100 MHz, DMSO): δ 29.1, 29.6, 34.3, 43.9, 55.3, 59.0, 61.3, 102.3, 102.5, 110.9, 113.1, 120.1, 126.8, 127.2, 130.0, 132.1, 146.3, 146.7, 178.6. LCMS (ESI+): m/z 407 (MH$^+$). Anal. Calcd. for C$_{25}$H$_{33}$N$_7$O$_6$: C, 56.92%; H, 6.30%; N, 18.58%; O, 18.20%. Found: C, 56.23%; H, 6.31%; N, 18.33%; O, 18.63%.

Characterization data of the tromethamine salt is summarized as follows:

(a) X-ray powder diffraction analysis (XRPD) [Inel XRG-3000 w/ CPS detector w/2θ range of 120°] indicated that the salt is in crystalline form (See FIG. 1);

(b) Differential scanning calorimetry (DSC) [TA Instruments 2920 or Q1000] analysis showed a melting endotherm range of 202-211° C., followed by decomposition;

(c) Thermogravimetric (TG) analysis. [TA Instruments 2050 or 2950] indicated 0.3-1% weight loss of the salt at 150° C.;

(d) Thermogravimetry-fourier transform spectroscopy (TGIR) analysis showed a small weight loss (<1%) corresponding to water;

(e) Vapor sorption analysis (DVS) [VTI SGA-100 Analyzer] showed that the salt displays low hygroscopicity of 2-4% at 90-95% RH;

(f) Optical microscopy (OM) [Leica DM LP] analysis indicated that the salt appears to be mostly tiny rods and birefringence is seen by cross polarized microscopy; and (g) The solubility of the salt was approximately 6 mg/mL in water.

(h) Stability data: no significant degradation was observed after 30 days at 40° C. and 75% RH.

A polymorph screen of the tromethamine salt indicated that after seven days of ambient temperature slurrying in ten different solvents, tromethamine salt sample XRPD patterns were consistent with that of the starting material (Table I) and were substantially similar to FIG. 1. Furthermore, the tromethamine salt form remained constant after refluxing the tromethamine salt starting material in IPA for 24 hrs.

TABLE I

| Solvent | Conditions | Observation | XRPD Form |
|---|---|---|---|
| DCM | RT Slurry, 7 d | Needles | Crystalline |
| THF | | Needles | Crystalline |
| MEK | | Needles | Crystalline |
| Heptane | | Needles | Crystalline |
| ACN | | Needles | Crystalline |
| TFE | | Blades/Rods | Crystalline |
| Toluene | | Needles | Crystalline |
| EtOH | | Needles | Crystalline |
| IPA:H$_2$O (1:1) | | Needles | Crystalline |
| H$_2$O | | Needles | Crystalline |
| IPA | Reflux, 1 d | Needles | Crystalline |

Example 2 trans-4-[4-amino-5-(7-methoxy-1H-indol-2-yl)imidazo[5,1-f][1,2,4]triazin-7-yl]cyclohexane carboxylic acid calcium salt Sodium trans-4-[4-amino-5-(7-methoxy-1H-indol-2-yl)-imidazo[5,1f][1,2,4]triazin-7-yl]-cyclohexanecarboxylate (201 mg, 0.469 mmol) was dissolved in water (2.00 mL) and heated to reflux. Calcium dichloride (51.8 mg, 0.467 mmol) was added and a solid immediately precipitated. The reaction was cooled to RT and filtered. The solid was washed with water and dried in vacuo at 60° C. to provide the title compound as a tan solid (180 mg, 90% yield). $^1$H NMR (400 MHz, DMSO): δ 1.67 (dddd, J=12.8, 12.8, 12.8, 2.8 Hz, 2H), 1.87 (dddd, J=13.2, 13.2, 13.2, 3.2 Hz, 2H), 2.14-2.17 (m, 4H), 2.34 (tt, J=12.4, 2.8 Hz, 1H), 3.40 (tt, J=12.4, 3.2 Hz, 1H), 3.65 (s, 6H), 4.01 (s, 3H), 6.75 (d, J=7.2 Hz, 1H), 6.75 (s, 1H), 7.04 (dd, J=7.6, 7.6 Hz, 1H), 7.23 (d, J=7.6 Hz, 1H), 7.88 (s, 1H).

Characterization data of the calcium salt is summarized as follows: (a) X-ray powder diffraction analysis (XRPD) indicated that the salt is crystalline (See FIG. 2); (b) Differential scanning calorimetry (DSC) analysis showed broad endotherms at 145.5° C. and 178.2° C.; (c) Vapor sorption analysis (DVS) showed that the salt displays hygroscopicity of 35% weight gain from 0 to 95% RH; and (d) Solubility was <1 mg/mL in water.

Example 3 trans-4-[4-amino-5-(7-methoxy-1H-indol-2-yl)imidazo[5,1-f][1,2,4]triazin-7-yl]cyclohexanecarboxylic acid sodium salt trans-4-[4-Amino-5-(7-methoxy-1H-indol-2-yl)-imidazo[5,1f][1,2,4]triazin-7-yl]-cyclohexanecarboxylic acid (10 g, 24.6 mmol) was suspended in de-ionized water (100 mL). A solution of aq. NaOH (prepared from 50% NaOH (1.97 g, 24.6 mmol) and de-ionized water (20 mL)) was charged over 10 min with stirring under nitrogen. A clear brown solution formed with pH ~0.8. Charcoal (0.5 g, 5 wt %) was charged. The mixture was stirred over 5 min and filtered through a glass microfiber (GF) and a paper (double) filter under gentle vacuum. The flask and the funnel were rinsed with small amount of de-ionized water. The brown filtrate was concentrated under reduced pressure at 30-35° C. Resulting sticky solids were kept under vacuum at 40-45° C. (water bath) over 30 min to get practically dry residue which can be transferred onto a drying tray. The solids were dried in a vacuum oven at 50° C. over 5 h to give the title compound as a tan solid (10.1 g, 96% yield). $^1$H NMR (400 MHz, DMSO): δ 1.43 (dddd, J=12.6, 12.8, 12.8, 2.4 Hz, 2H), 1.68 (dddd, J=12.4, 12.4, 12.4, 2.8 Hz, 2H), 1.99-2.02 (m, 5H), 3.12 (tt, J=12.0, 2.8 Hz, 1H), 3.92 (s, 3H), 6.61 (d, J=7.6 Hz, 1H), 6.67 (s, 1H), 6.88 (dd, J=7.6, 7.6 Hz, 1H), 7.12 (d, J=8.0 Hz, 1H), 7.72 (s, 1H). Anal. Calcd for C$_{21}$H$_{21}$N$_6$O$_3$Na.H$_2$O: C, 56.50%; H, 5.19%; N, 18.82%; Na, 5.15%. Found: C, 56.44%; H, 4.76%; N, 18.51%; Na, 4.55%.

Characterization data of the sodium salt is summarized as follows: (a) X-ray powder diffraction analysis (XRPD) indicated that the salt is mostly amorphous; (b) Differential scanning calorimetry (DSC) analysis showed a broad endotherm at 98.3° C., and exotherms at 224.1° C. and 256.8° C.; (c) Thermogravimetric (TG) analysis indicated 3.8% weight loss of the salt at 250° C.; (d) Vapor sorption analysis (DVS) showed that the salt displays hygroscopicity of 37% weight gain from 0 to 95% RH; and (e) The solubility was >30 mg/mL in water.

Example 4 trans-4-[4-amino-5-(7-methoxy-1H-indol-2-yl)imidazo[5,1-f][1,2,4]triazin-7-yl]cyclohexanecarboxylic acid L-arginine salt trans-4-[4-Amino-5-(7-methoxy-1H-indol-2-yl)-imidazo[5,1-f][1,2,4]triazin-7-yl]-cyclohexanecarboxylic acid (11.1 g, 27.4 mmol) and L-arginine (5.72 g, 32.9 mmol) were diluted with H$_2$O (78.0 mL) and EtOH (78.0 mL). The suspension was heated to reflux to give a clear solution and then cooled to RT slowly. After 16 h, the suspension was cooled in an ice bath for 30 min and then filtered. The off-white solid was dried in vacuo at 80° C. for 2 days for provide the title compound (12.9 g, 81% yield). $^1$H NMR (400 MHz, CD$_3$OD): δ 1.59-1.78 (m, 3H), 1.79-1.90 (m, 3H), 2.13 (br d, J=10.8 Hz, 4H), 2.35 (tt, J=12.4, 3.6 Hz, 1H), 3.20-3.42 (m, 1H), 3.37 (tt, J=12.0, 2.8 Hz, 1H), 3.66 (br s, 4H), 3.98 (s, 3H), 6.72 (d, J=7.6 Hz, 1H), 6.72 (s, 1H), 7.01 (dd, J=8.0, 8.0 Hz, 1H), 7.22 (d, J=8.4 Hz, 1H), 7.84 (s, 1H). X-ray powder diffraction analysis (XRPD) indicated that the salt is amorphous.

The invention claimed is:

1. A pharmaceutically acceptable salt of trans-4-[4-amino-5-(7-methoxy-1H-indol-2-yl)imidazo[5,1-f][1,2,4]triazin-7-yl]cyclohexane carboxylic acid, wherein the salt is selected from sodium, calcium, L-arginine, magnesium, potassium, N,N-diethylethanolamine, N-methyl-D-glucamine, or tromethamine.

2. The salt of claim 1, wherein the salt form is selected from sodium, calcium, or L-arginine.

3. The salt claim 1, wherein the salt form is selected from magnesium, potassium, N,N-diethylethanolamine, or N-methyl-D-glucamine.

4. The salt of claim 1, wherein the salt form is tromethamine.

5. The salt of claim 4, which is a tromethamine salt hydrate or solvate form.

6. The salt of claim 1, which is in substantially amorphous form.

7. The salt of claim 4, which is in substantially crystalline form.

8. The salt of claim 4, which is present in an amount that is at least about 95% by weight crystalline.

9. The salt of claim 4, which is present in an amount that is substantially a single crystalline form.

10. The salt of claim 4 which degrades by about 1% by weight or less during 30 days at 40° C. and 75% RH.

11. The salt of claim 4, which exhibits a $^{13}$C NMR spectrum (100 MHz, DMSO) with peaks at or near: $\delta$ 29.1, 29.6, 34.3, 43.9, 55.3, 59.0, 61.3, 102.3, 102.5, 110.9, 113.1, 120.1, 126.8, 127.2, 130.0, 132.1, 146.3, 146.7, 178.6.

12. The salt of claim 4, which has a hygroscopicity of about 2-4% at 90-95% RH.

13. The salt of claim 4, which exhibits a sharp endotherm at about 202-211° C. via DSC analysis.

14. The salt of claim 4 which has a solubility in water of at least about 6 mg/mL.

15. The salt of claim 4 which when subjected to 30 days at 40° C. and 75% RH decomposes by about 1% by weight or less during.

16. The salt of claim 1, which is a tromethamine salt that exhibits an X-ray powder diffraction pattern having peaks (°2θ) at about 5.5, 7.7, 10.7, 14.5, 15.5, 23.0, and 25.5 using an Inel XRG-3000 with CPS detector with 2θ range of 120°.

17. A pharmaceutical composition comprising a salt of claim 4 formulated with or without at least one pharmaceutically acceptable excipient.

18. A method of treating lymphoma or ovarian cancer comprising administering to a patient in need thereof an effective amount of a salt of claim 4.

* * * * *